United States Patent [19]

Godeux

[11] 4,215,574

[45] Aug. 5, 1980

[54] INDICATION OF THE MOMENTARY VALUE OF LIQUID LEVEL

[75] Inventor: Michel Godeux, Bougival, France

[73] Assignee: Claude A. Patalidis, Lathrup Village, Mich.; a part interest

[21] Appl. No.: 958,404

[22] Filed: Nov. 7, 1978

[30] Foreign Application Priority Data

Nov. 8, 1977 [FR] France ................................. 7733594

[51] Int. Cl.² ............................................. G01F 23/08
[52] U.S. Cl. ....................................... 73/314; 73/307; 73/322.5; 116/205
[58] Field of Search ................. 73/314, 315, 320, 322, 73/432 A, 307; 116/228, 205

[56] References Cited

U.S. PATENT DOCUMENTS

| | | | |
|---|---|---|---|
| 1,685,051 | 9/1928 | Girardet | 73/314 |
| 1,858,411 | 5/1932 | Muzzy | 73/315 X |
| 1,911,555 | 5/1933 | De Orlow | 73/314 |
| 1,925,747 | 9/1933 | Caretta | 73/314 |
| 3,138,024 | 6/1964 | Pariser et al. | 73/308 |

FOREIGN PATENT DOCUMENTS 268660 10/1929 Italy ......................................... 73/314

*Primary Examiner*—Daniel M. Yasich
*Attorney, Agent, or Firm*—Hauke and Patalidis

[57] ABSTRACT

An apparatus and method for checking and measuring the momentary value of a variable physical magnitude, such as a volume of liquid in a container or tank, or a temperature, viscosity, or velocity, for example. The invention comprises a transducer free to follow without friction the variations of the physical magnitude, such as for example the level of a liquid fluid in a reservoir, the transducer having a portion of progressively varying cross-section displaceable as a function of the changes in the physical magnitude disposed in alignment with a sensor normally positioned in a reference position out of contact from the transducer. When a checking or measurement is desired, the sensor is displaced in engagement with the varying cross-section portion of the transducer, and the amount of displacement of the sensor from its reference position to its position of engagement with the transducer represents the instantaneous position of the transducer and therefore the momentary value of the magnitude, such as the level of a liquid, to be checked or measured.

16 Claims, 8 Drawing Figures

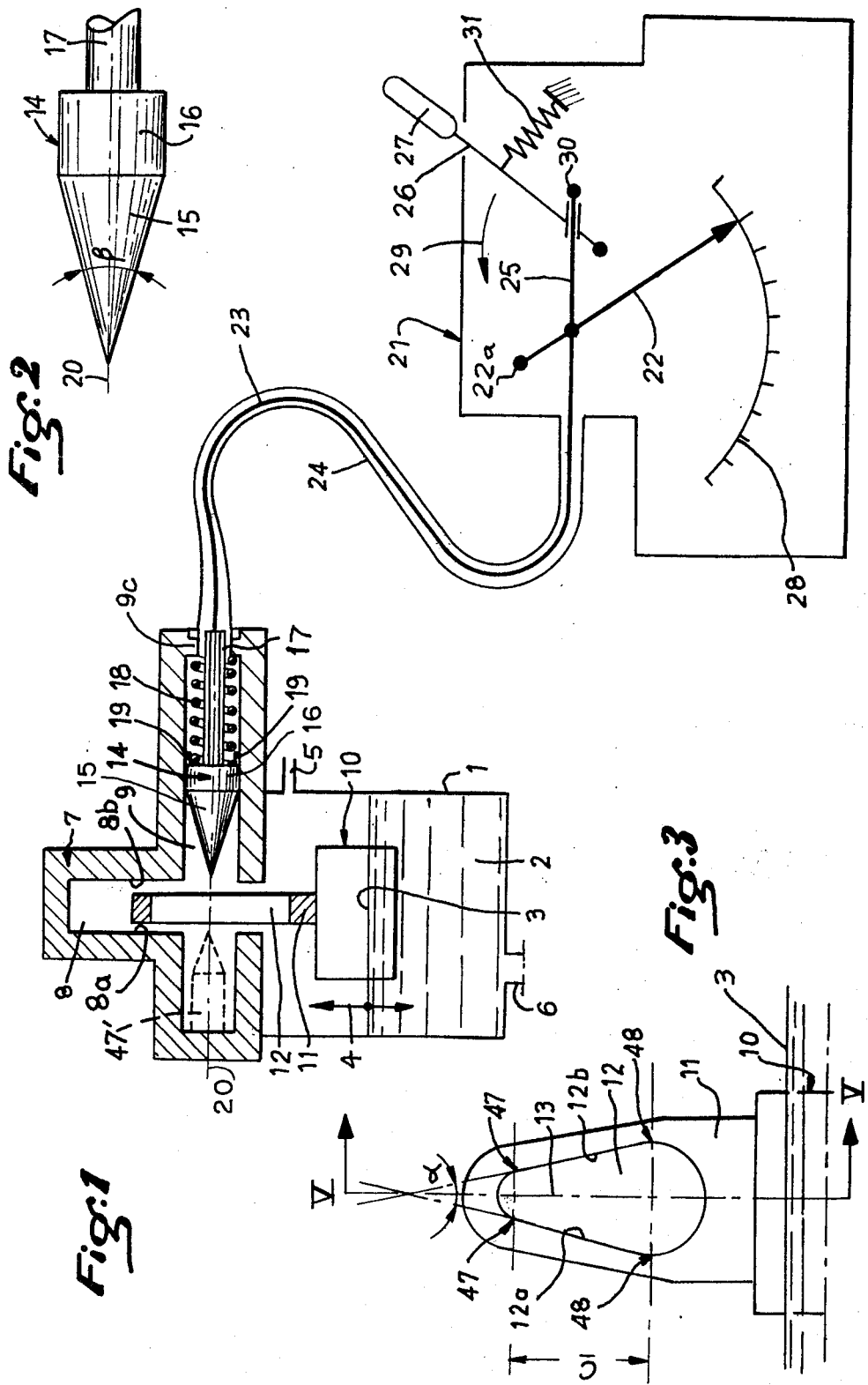

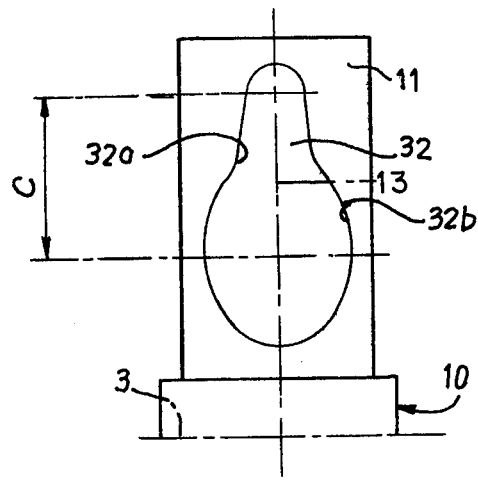
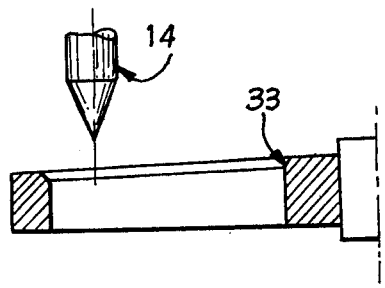
Fig. 4
Fig. 5
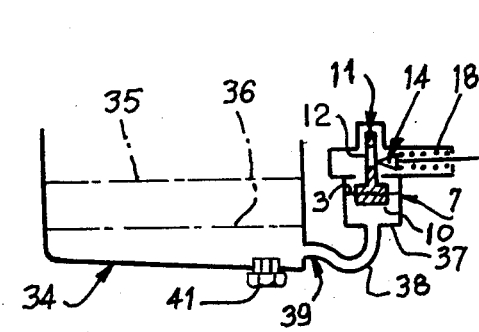
Fig. 6
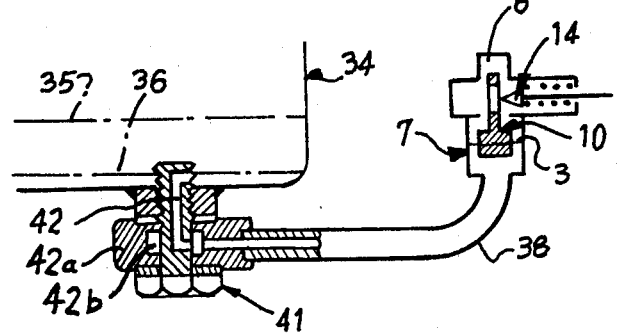
Fig. 7

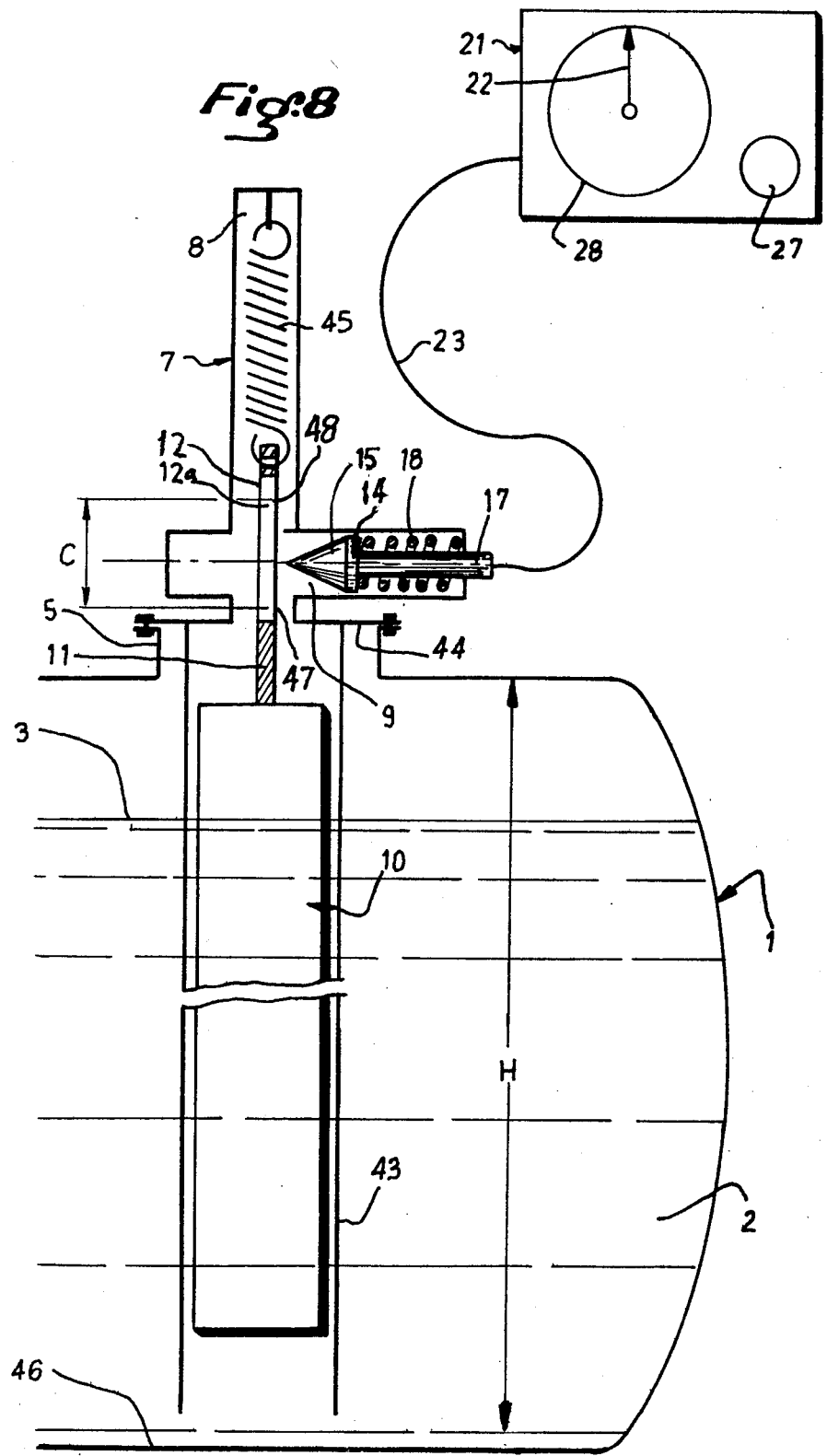

INDICATION OF THE MOMENTARY VALUE OF LIQUID LEVEL

BACKGROUND OF THE INVENTION

The present invention relates to an apparatus for checking and measuring the momentary value of a variable physical magnitude such as the volume of a liquid in a container or tank, a temperature, viscosity, or a velocity, for example. The present invention also relates to a method providing a real time indication of the momentary value of the variable physical magnitude, and also to an enclosure or tank containing a liquid and provided with such device.

For the purpose of monitoring, or for safety or maintenance reasons, among others, there is often present a requirement, as is well known, for obtaining a quantitative indication, either by a simple level indicator or better yet by a more precise volumetric indicator of the absolute value of certain physical parameters tied to a variable factor such as elapsed time, or the available volume of a liquid in a reservoir of small capacity, such as the lubricating oil contained in the crankcase of an internal combustion engine or in the transmission housing of a motor vehicle or, on the contrary, of the liquid contained in a large capacity tank, reservoir or cistern, containing several thousand liters of liquid.

Devices for that purpose, made according to modern day technology, and which permit to give an indication of the level or to measure the variations in such quantities, provide a relatively weak signal at their output which is of little use without amplification requiring auxiliary energy sources.

The result is that such devices have poor sensitivity and accuracy unless they call upon auxiliary energy sources, and when they are provided with an amplification device, they become rather complex and are therefore somewhat costly to manufacture.

The principal object of the present invention is to remedy the inconveniences of the prior art and to provide a method and apparatus for supplying an indication of the momentary instantaneous value of a variable physical magnitude, by simple means and thus at a relatively low cost, and which is nevertheless sturdy and reliable such as to cut down on maintenance costs. In addition, a device according to the invention does not depend on the existence of auxiliary energy sources, while still permitting checking or monitoring at a remote location.

It will be appreciated that an apparatus according to the present invention comprises elements which are completely free to move, that is which are entirely independent of mechanical, magnetic or electrical connections, for example. The result is that such a freedom of motion provides the device of the invention with considerable sensitivity and accuracy which, as is evident, are basic qualities for any type of measuring instruments.

The object of the present invention therefore is to provide a device capable of giving an indication of the momentary value of a variable physical magnitude characterized in that it comprises a movable transducer in engagement with the physical characteristics to be measured and able to be freely displaced according to the smallest variation of said magnitude in opposite or alignment with a sensor in a rest or reference position, the transducer having a portion of varying cross-section displaceable opposite the sensor. Means are provided for displacing the sensor relative to the transducer to engage the sensor with the transducer as well as means for indicating the position of the sensor when in engagement with the transducer and for returning the sensor to its reference position.

According to a preferred embodiment, the device further comprises means for measuring the amount of displacement of the sensor between its reference position and its position in engagement with the transducer, said means being coupled directly or indirectly to the sensor, means for engaging the sensor with the transducer, such means for engaging the sensor with the transducer consisting of a spring and the sensor having a portion having a progressively varying cross-section on its full length capable of engaging the transducer at the portion of the transducer having itself a varying cross-section, the line of sight of the variation of the cross-section of the transducer and of the sensor being in a plane perpendicular to the axis of displacement of the sensor, the transducer and the sensor having one a female member and the other a male member of varying cross-sections complementary of each other, the engagement of the sensor against the transducer being effected through such members, male and female, the male member of the transducer-sensor arrangement being a cone having an axis parallel to the direction of displacement of said members, and the female member being a window formed in alignment with the male member, the width of the window varying from an end to the other and the edges of the window engageable with the male member being provided with a bevel or chamfer.

In a particularly advantageous structure, in which the female member is integral with the transducer and the male member is integral with the sensor, the female member is a window formed in a plate disposed between the two spaced-apart parallel walls of a housing and displaceable in unison with the transducer under the influence of the variations of the magnitude to be checked or monitored, and the sensor is urged toward the transducer in a direction substantially perpendicular to said walls which act, for the transducer-sensor assembly, as abutments when the two co-operating parts of the structure respectively engage and disengage.

A further object of the present invention is to provide a method for giving an indication of the momentary or instantaneous magnitude of a variable physical quantity characterized in associating the motion of a movable transducer with the variations of the magnitude to be measured, the transducer not touching any other element and being entirely free to be displaced when subjected to the minutest variation of said magnitude, in urging a sensor toward said transducer until a male member of one engages into a female member of the other, the female and male members having varying sections which are respectively complementary of each other, and in providing an indication of the position of said sensor when in engagement with the transducer.

Finally, the present invention has for object to provide a container or tank such as the crankcase of a motor vehicle, or any other reservoir or tank, provided with the device of the invention.

The many objects and advantages of the present invention will become readily apparent when the following description of the best modes contemplated for practicing the invention is read in conjunction with the accompanying drawing, giving examples of structures for illustrative purpose only and not for the purpose of limitation, and in which:

BRIEF DESCRIPTION OF THE DRAWING

FIG. 1 is a schematic representation of an example of structure according to the present invention in which the transducer is a float arranged to measure the level of a liquid contained in a reservoir;

FIG. 2 is a side view of a sensor according to the invention;

FIGS. 3 and 4 are front elevation views of two different examples of transducer structures;

FIG. 5 is a section along a line V—V of the transducer of FIG. 3;

FIG. 6 is another example of a schematic representation of a device according to the invention in which the transducer is a float arranged to indicate the level of lubricating oil contained in the crankcase of a motor vehicle engine;

FIG. 7 is a further example of a schematic representation of a device according to the invention wherein the transducer is a float arranged to indicate the level of lubricating oil in an internal combustion engine crankcase; and FIG. 8 is a further example of a schematic representation of structure according to the present invention, in which the transducer is a float arranged to measure the level of a liquid contained in a large capacity tank.

DETAILED DESCRIPTION OF THE PREFERRED EMBODIMENTS

In the following description, the example of applications of the invention which has arbitrarily been chosen, for illustrative purpose, is that of a device for giving an indication of the level or volume of a liquid in an enclosure, the movable transducer being a float.

It will be readily apparent however that such an example of applications of the invention is not intended to be limitative, and that by simply changing the type of transducer used, the principle of the invention is applicable generally to means for checking or measuring a multitude of variable physical magnitudes, other than a level or volume of liquid. For example, for measuring temperature the float is replaced by a bi-metallic element. For measuring wind velocity, for example, the float is replaced by an anemometer having a vane inclinable as a function of the wind velocity to be measured.

Referring now to FIG. 1, there is illustrated a reservoir 1 containing a liquid 2 having a level 3 capable of rising or, on the contrary, dropping, as arbitrarily shown by the arrow 4, according to whether more liquid is added through the reservoir inlet 5 or drained through the outlet 6. The height of the level of the liquid is the variable physical magnitude which is to be checked or measured.

A housing 7 is disposed on top of the reservoir 1. A pair of chambers 8 and 9, respectively, are formed within the housing 7, the two chambers 8 and 9 being respectively parallel and perpendicular to the direction of variation of the level of liquid, i.e. respectively parallel and perpendicular to the vertical.

The variable physical magnitude or quantity to be measured is associated directly to a transducer which, for the particular application contemplated, is a float 10 which inherently participates closely with the magnitude to be checked or measured and follows rigorously its smallest variations. The float 10 comprises a base, having a parallelepipedonal shape for example, provided on its top with a plate 11 upwardly extending vertically into the interior of the vertical chamber 8 in the housing 7, the left wall 8a and the right wall 8b of the chamber 8 being spaced apart from each other to a sufficient distance to enable the plate 11 to be freely displaceable, that is without contact with the inner surface of the chamber 8.

The plate 11 has a transverse aperture in the form of a window 12 having inner edges disposed symmetrically relative to the vertical axis 12, FIGS. 3 and 4, the width of the window 12 varying from top to bottom; in the structure of window 12 illustrated, for example at FIG. 3, the window 12 has a semi-oval shape with rectilinear sides 12a and 12b, respectively, symmetrically disposed at an angle relative to the vertical axis 13, thus limiting to a height C the useful travel of the float 10.

A feeler or sensor 14 is disposed within the chamber 9 which extends along a horizontal axis, the sensor 14 being provided with a conical end portion 15, as shown also at FIG. 2, having its apex disposed toward the window 12, the base of the conical portion 15 forming a circularly cylindrical body portion 16 freely slidable in the bore forming the chamber 9. The other end of the sensor 14 is in the form of a cylindrical rod 17 integral with or fastened behind the sensor cylindrical body portion 16 and acting as a pilot for a coil spring 18 compressed between the rear surface of the cylindrical body portion 16 and the end wall 9c of the chamber 9. The travel of the sensor 14 is limited in one direction by a fixed annular abutment 19 disposed on the surface of the horizontal chamber 9, and in the other direction by the inner edges of the frame of the window 12.

In this respect, it will be appreciated that the conical end portion 15 of the sensor 14 defines a male member having a progressively varying cross-section for each of an infinity of imaginary planes perpendicular to a horizontal axis 20, which also defines the longitudinal axis of displacement of the sensor 14 within the chamber 9. Similarly, the width of the window 12, as best shown at FIG. 3, progressively varies for each imaginary plane cutting the vertical axis 13 of displacement of the window or for each plane of sighting through the window, the vertical axis 13 being obviously parallel to the arrow 4 of FIG. 1. The conical end portion 15 of the sensor 14, which defines a male member, is complementary of a female member, namely the window 12. In other words, the maximum width of the window 12 between its inner edges 12a and 12b is slightly smaller than the diameter of the base of the conical end portion 16. Because of the relative dimensions of the elements, when the sensor 14 is urged toward the plate 11 the apex of its conical end portion 16 projects through the window 12 until the side surface of the conical portion abuts on the opposite of the side edges 12a and 12b of the window.

The sensor 14, when disengaged from its rest or reference position in engagement with the annular abutment 19 by means explained hereinafter in detail, is urged horizontally towards the transducer, defined by the float 10 provided with the window 12 in the float plate 11, under the action of the coil spring 18, with a force which may be as small or as large as desired.

It will be noted that the distance travelled by the sensor 14 between its rest or reference position and its position of engagement within the window 12 is an analytical representation of the position of the transducer, or float 10, at the instant of engagement between the transducer and the sensor. It is evident that, because of the constantly variable geometric shape given to the window 12 and to the conical end portion 15 of the sensor 14, it is possible to analytically translate, by appropriate choice of those geometric shapes, each position occupied by the transducer, each such position being itself closely related to the momentary value of the physical magnitude to be measured which is, in the example illustrated, the level 3 of the liquid 2 in the reservoir 1.

In other words, the variations in altitude of the float 10, which variations faithfully represent the variations of the level 3, are translated along a horizontal plane to the position of abutment of the sensor 14 within the window 12, such abutment position being capable of instantaneously notation or checking or, in the alternative, being capable of being interpreted by measuring the distance travelled by the sensor between its rest or reference position and its position of abutment within the window.

In its simplest form, the interpretation of the position of the sensor, when in abutting engagement within the window, provides an indication or information, by "all or nothing", as to whether the height of the liquid 2 in the reservoir 1 is sufficient, or on the contrary insufficient. Another application of this form of indication in its simplest form is to provide an indication of the height of the level of lubricating oil contained in a housing or in an oil tank in a motor vehicle or the like.

It is also equally of interest to complete the above explained simple indication of the position occupied by the sensor relative to the transducer by a measure of the distance travelled by the sensor, this distance being a function of the variation of the physical magnitude to be measured. For that purpose, an indicating instrument 21 is associated with the above described structure, the indicating instrument being of the type provided with a pointer 22, or a ribbon or disk, and a link 23, either flexible or rigid, protected by an enclosing sheath 24 connecting the rod 17 of the sensor 14 to the movable indicating means of the instrument 21, that is to the pointer 22 in the example of structure shown at FIG. 1. In such a structure, the static energy of the spring 18, which plays the role of prime mover for the sensor 14, is used not only for causing the motion of the sensor but also for driving the movable member of the indicating instrument.

The link 23 is preferably provided with an extension, as shown at 25, connected to a lever 26 provided with a manually operable locking arrangement such as to be locked in a rest position by means of a control knob 27. In order to take a measurement of the variation of the physical quantity to be measured, the knob 27 is actuated which results in freeing the link 23-25. This in turn results in freeing the sensor 14 for travel towards the window 12, under the action of the spring 18. When the sensor is in abutting engagement against the transducer, namely when the conical end portion 15 is in the window 12, the position of the sensor is indicated by the indicating instrument 21 by way of the angular position of the pointer 22 pivotable about a pivot 22a relative to a scale 28.

As soon as a reading has been noted, as arbitrarily represented by the arrow 29 indicating the displacement of the lever 26, the sensor 14 is brought back to its initial rest or reference position by swinging the lever 26 until it engages an abutment 30. A return spring 31, opposing the constant bias of the coil spring 18 in an opposite direction, aids in returning the lever 26 to its rest position.

According to an alternate structure of the invention, the return spring 31 is stronger than the coil spring 18. Under those conditions, the natural rest position of the lever 26 is that represented at FIG. 1, the release knob 27 being therefore unnecessary. Reading by means of the indicating instrument 21 is effected by swinging the lever 26 in the direction of the arrow 29 to enable the spring 18 to operate the sensor 14, and after a reading has been effected, the lever 26 is released and is automatically returned to its rest position.

Referring now to FIGS. 2 and 3, it is to be noted that the angle $\alpha$ between sides 12a and 12b of the window 12 and the angle $\beta$ of the conical end portion 15 of the sensor 14 have respective values which have been chosen to ensure a good stability of the elements during detection of the vertical position of the window 12 when the sensor, allowed to travel towards the window, is in abutting engagement within the window 12. The angles $\alpha$ and $\beta$ are determined to ensure an appropriate engagement between the conical end portion 15 of the sensor and the inner edges of the frame of the window 12, and to ensure that the two elements, male and female, are easily separated without wedging into each other.

With the side edges 12a and 12b of the window 12 being rectilinear, and the male member being a cone, the reading on the indicating instrument 21 is simply proportional to the variation in altitude of the float 10, therefore is proportional to the variation of the level 3 of the liquid 2, which is the physical magnitude being measured.

However such a shape for the male and female members, as illustrated, should not be considered as being limitative. For example, a window as shown at 32 at FIG. 4 could be used, having lateral edges 32a and 32b each of a substantially S-shape contour which compensates for the non-proportional indication obtained while checking or measuring the level of a liquid contained, for example, in a spherical tank.

Further, in order to ensure a substantial accuracy of the device of the invention, the edges of the window 12 engaging the conical portion of the sensor are beveled or chamfered as shown at 33, FIG. 5, which prevents the conical end portion of the sensor from wedging itself in the window, or deforming the window edges at the points of engagement between the elements. In addition, forming a peripheral chamfer at the same angle as the surface of the conical end portion 15 provides engagement between the elements along two lines rather than at two points, which in turn results in a more accurate reading.

Referring again to FIG. 1, it will be seen that the sidewalls 8a and 8b of the vertical chamber 8 act as support surfaces when the conical end portion 15 of the sensor 14 engages the window 12, or disengages from the window. In addition, the spring 18 which applies a constant pressure on the sensor 14, independently of the control of the operator of the device, presents the advantage of avoiding subjecting the float to excessive stress. The float is therefore entirely free to follow the variations of the physical quantity to be measured, such that absolute precision of the measurement is achieved.

The indicating instrument 21 may be remotely located, in view of the flexible or rigid connection 23, but it can also be directly coupled to the rod 17 extending from the sensor 14. Alternatively, a different type of transmitting means may be used such as for example a fluid transmission, that is a device comprising a pair of deformable or movable walls between which is disposed a constant volume of a non-compressible fluid.

FIG. 6 represents a modification of the device of the invention for checking or detecting the level of lubricating oil in the crankcase 34 of a motor vehicle engine. It is known that the level of lubricating oil in the crankcase of an internal combustion engine crankcase must be maintained between a maximum or overfill level 35 and a minimum or danger level 36 below which the oil level should not fall.

In the structure of FIG. 6, the housing 7 is mounted proximate the crankcase 34 and is provided at its bottom 37 with a conduit 38 connected to a fitting 39 disposed at the bottom of the crankcase 34. The crankcase 34 is also provided at its bottom with a conventional drain plug 41.

The vertical position of the float 10 in the housing 7 is, as hereinbefore explained, interpreted by the position of the sensor 14 whose male member penetrates more or less within the female member 12 of the float. A housing 40 comprising the push-button 27 and the indicator dial 28 is mounted on the instrument panel of the motor vehicle and is connected to the sensor 14 by means of the flexible link 23.

The level of lubricating oil in the housing 7, which is the same as the level of lubricating oil in the crankcase 34, is translated to the indicator dial 28 in the housing 40 and is represented by the position of the pointer, not shown, which position is a function of the amount of penetration of the sensor 14 within the window 12 of the float 10 at the exact moment a reading is taken.

In the arrangement illustrated at FIG. 7, the fitting 39 at the bottom of the crankcase 34 of FIG. 6 is replaced by a fitting built in the crankcase drain plug 41. The body of the drain plug 41 is modified such as to be provided with a passageway 42 placing the housing 7 in communication with the interior of the crankcase 34 by means of the conduit 38 provided on its end with an appropriate flat cylindrical connecting member 42a having an interior annular space 42b placing the drain plug passageway 42 in communication with the conduit 38. The housing 7 contains the device of the invention hereinbefore explained in detail.

In the two embodiments above-described, it will be appreciated that the action of the push-button 27 on the connection between the sensor 14 and the indicator pointer is effected through the intermediary of an abutment such as the abutment 30 of FIG. 1. When it is desired to take a reading, the push-button 27 is manually pulled to the end of its stroke, thus causing the sensor-pointer arrangement to provide a reading when the sensor engages the float window.

In the embodiment of FIG. 8, which provides a reading of the level of a liquid 2 in a large capacity tank 1, the float 10 is disposed within a stationary protecting tubular member 43 extending from the top of the tank, flush with its cover 44, to proximate the bottom 46 of the tank 1. The float plate 11 is attached to the end of a weight compensating tension spring 45 mounted in the vertical chamber 8 of the housing 7 affixed to the top of the tank cover 44.

The float 10 is therefore subjected to three forces: its weight P which is constant, the pull of the spring 45, and the force exerted vertically on the float by the liquid 2, which is a function of the volume and density of the liquid displaced by the submerged portion of the float.

The maximum force exerted on the float 10 which corresponds to the maximum volume of the float that can be submerged within the liquid can be calculated for a liquid of a known density. The float 10 is selected with a weight P balancing the floatation force exerted on the float, and has a length which is equal to the height H of permissible variation of the level of liquid 2 in the tank 1, decreased by the permissible stroke C corresponding to the design of the window 12 of the float. The spring 45 is chosen with a ratio such that the spring extends, under the action of the weight of the float 10, only to a distance corresponding to the useful stroke C of the float window.

Under those conditions:

(a) When the level of the liquid 2 in the tank 1 is maximum, the float 10 is at its highest position, the surface of the conical end 15 of the sensor 14 engages the side edges of the window 12, such as the side edges 12a and 12b of FIG. 3, at two opposite points 47, and the spring 45 is in its shortest state, (b) When the level of the liquid 2 inside the tank 1 is at its lowest level, the float 10 is in its lowest position with its bottom engaging the bottom 46 of the tank, the surface of the conical end 15 of the sensor 14 is engageable in the window 12 at two opposite points 48 of its side edges, such as the side edges 12a and 12b of FIG. 3, because the spring 45 is subjected to a force causing it to extend the full distance C.

It will be appreciated by those skilled in the art, from the description of the invention herein, that the many advantages of the objects of the invention are accomplished, namely:

The movable transducer, whose position is monitored, is entirely free to reciprocate vertically up and down and down and up, because it is not subjected to any force resulting from mechanical, magnetic or electrical connections, except at the precise moment when it is desired to know its exact position and when it defines an abutment for the sensor 14. The absolute freedom of motion of the transducer ensures that the device of the invention is endowed with substantial sensitivity as well as accuracy;

The diverse co-operating elements of the device of the invention are exclusively mechanical elements, therefore sturdy and easy to manufacture, which result in a very low manufacturing cost and minimal maintenance;

Although the device enables remote reading, it does not use any auxiliary source of energy.

It will also be appreciated that the invention is not limited to the disclosed applications and embodiments and that diverse modifications of the invention will be evident to those skilled in the art within the scope of the invention. For example, the material of which the transducer is made may be chosen such as to be appropriate to the ambient with which it is in direct contact, such as corrosive chemical solutions, atmospheric air, or a fluid at high temperature, for example. It will also be appreciated that because checking or measuring of the instantaneous value of the variable physical magnitude results from locking in position the transducer at the precise moment a reading is effected, it is easy and not costly at all to provide a substantial amplification gain by mechanical means which can be used in dangerous, corrosive, noxious or explosive surroundings.

As a first example of modification of structure, the abutment 19, FIG. 1, may advantageously take the form of an electro-magnet controlled by the push-button 27;

with such a structure, a pull exerted on the sensor 14 by the electro-magnet disappears at the moment the control button 27 is actuated, and the sensor is attracted and held in its rest or reference position as soon as the lever 26 is positioned in its locked position shown at FIG. 1. Such an arrangement presents many advantages where it is difficult to provide a mechanical transmission, such as the mechanical transmission 23-25 illustrated. In order to know the position of the sensor against the transducer window after unlocking the sensor by means of the electro-magnet, the sensor may be provided with appropriate electrical contacts.

As a second example of modification, providing a particularly simple structure, it is a simple matter to substitute for the indirect coupling between the indicating means and the sensor a direct coupling by connecting the rod 17 of the sensor 14 to the control means 26-27, and in observing the displacement of the control means whose stroke is exactly representative of the displacement of the sensor. With such an arrangement, the spring 18 may be omitted because the manual operation of the control means directly engages the sensor with the transducer and, after a reading is effected, it permits to disengage the elements.

A third example of modification consists in providing the transducer with a male member, preferably in the form of a conical member disposed along a vertical axis with its apex directed upwardly. The position of the transducer is, in such a structure, read by means of a sensor provided with a female member, such as the window 12, or with a male member such as the sensor conical end portion 15, or even with sharp needle, whose correct engagement is ensured with the transducer when a reading is taken if the surface of the transducer is grooved all along its conical portion having a progressively decreasing cross-section, and which corresponds to the displacement of the transducer relative to the sensor.

A fourth example of modification, schematically illustrated in dash line at 47' at FIG. 1, consists in placing the sensor in the portion of the horizontal chamber 9 disposed, relative to the transducer, on the side opposite to the side where is disposed the engaging or measuring means. With such a structure, the sensor is not pushed towards the transducer, but it is pulled, by means such as the flexible connection 23, and is pushed away from the transducer after a reading has been taken.

Having thus described the present invention, by way of typical structural embodiments whereof, modification whereof will be apparent to those skilled in the art, what is claimed as new is as follows:

1. Apparatus for checking or measuring the momentary value of a variable physical magnitude comprising a movable transducer, means connecting said movable transducer to the physical magnitude to be checked or measured and displacing said transducer from a reference position as a function of any small variation of said magnitude, a portion of said transducer having a cross-section progressively varying as a function of the displacement of said transducer, sensing means in registry with said transducer portion and normally in a reference position away from said transducer, control means displacing said sensing means in abutting engagement with said transducer portion for selectively checking displacement of said transducer, indicator means providing an indication of the position of said sensing means when in engagement with said transducer portion, said control means selectively returning said sensing means to said reference position, and means measuring the amount of displacement of said sensing means between said reference position and said position in engagement with said transducer portion.

2. The apparatus of claim 1 wherein said portion of said transducer having a progressively varying cross-section is perpendicular to the axis of displacement of said transducer.

3. The apparatus of claim 1 wherein said means displacing said sensing means in engagement with said transducer portion is a spring.

4. The apparatus of claim 1 wherein said sensing means has a portion having a progressively varying cross-section engageable with said portion of said transducer having a progressively varying cross-section.

5. The apparatus of claim 4 wherein each of the cross-sections through said portion of progressively varying cross-section of said sensing means is disposed in a plane perpendicular to the axis of displacement of said sensing means.

6. The apparatus of claim 4 wherein said transducer and said sensing means are one a female member and the other a male member, said male member and said female member being provided each with one of said portions of varying cross-section and being respectively complementary of each other, the engagement of said sensing means with said transducer being effected through the intermediary of said female and male members.

7. The apparatus of claim 6 wherein said female member is mounted on said transducer and said male member is mounted on said sensing means.

8. The apparatus of claim 6 wherein said female member is a window in which said male member is engageable, the width of said window progressively varying from one end to the other.

9. The apparatus of claim 8 wherein the edge of said window engageable with said male member is chamfered.

10. The apparatus of claim 6 wherein said male member is a conical member having an axis of symmetry parallel to the axis of displacement of said male member.

11. The apparatus of claim 10 wherein said female member is a window in which said male member is engageable, the width of said window progressively varying from one end to the other.

12. The apparatus of claim 11 wherein the edge of said window engageable with said male member is chamfered.

13. The apparatus of claim 11 wherein said female member is a window disposed in a plate affixed to said transducer, said plate being disposed between two spaced apart parallel walls and said sensing means being displaced along an axis substantially perpendicular to said walls, said walls providing abutment means during engagement and disengagement of said sensing means in said window.

14. The apparatus of claim 1 wherein said variable physical magnitude is a volume of liquid in a container.

15. A method for checking the momentary instantaneous value of a variable physical magnitude, said method comprising displacing a transducer from a reference position as a function of the variation of said physical magnitude, said transducer having a first vertically displaceable portion and a second portion of a cross-section progressively varying as a function of said vertical displacement, selectively engaging the first portion of the transducer with said second portion of said transducer as the transducer is displaced, and noting the position of said sensor.

16. The method of claim 15 wherein the position of said sensor is noted by measuring the distance of displacement of said sensor between a reference position and its position of engagement with said transducer.

* * * * *

UNITED STATES PATENT AND TRADEMARK OFFICE
CERTIFICATE OF CORRECTION

PATENT NO. : 4,215,574
DATED : August 5, 1980
INVENTOR(S) : Michel Godeux

It is certified that error appears in the above-identified patent and that said Letters Patent are hereby corrected as shown below:

Column 4, line 10, change "axis 12" to --axis 13--.

Signed and Sealed this

Sixteenth Day of December 1980

[SEAL]

*Attest:*

SIDNEY A. DIAMOND

*Attesting Officer*     *Commissioner of Patents and Trademarks*